United States Patent
Chou et al.

(12) 
(10) Patent No.: US 6,236,044 B1
(45) Date of Patent: May 22, 2001

(54) METHOD AND APPARATUS FOR INSPECTION OF A SUBSTRATE BY USE OF A RING ILLUMINATOR

(75) Inventors: Mau-Song Chou; Richard A. Chodzko, both of Rancho Palos Verdes; L. Suzanne Casement, Fountain Valley; Jonathan W. Arenberg, Santa Monica, all of CA (US)

(73) Assignee: TRW Inc., Redondo Beach, CA (US)

( * ) Notice: Subject to any disclaimer, the term of this patent is extended or adjusted under 35 U.S.C. 154(b) by 0 days.

(21) Appl. No.: 09/138,230

(22) Filed: Aug. 21, 1998

(51) Int. Cl.[7] .................................................. G01N 21/88
(52) U.S. Cl. ........................ 250/330; 250/332; 250/493.1
(58) Field of Search .................................. 250/330, 332, 250/493.1

(56) References Cited

U.S. PATENT DOCUMENTS

| | | | |
|---|---|---|---|
| 3,841,920 | * 10/1974 | Martin ................................. | 148/6.35 |
| 4,501,966 | * 2/1985 | Forman et al. ....................... | 250/332 |
| 4,695,130 | 9/1987 | Medina . | |
| 4,792,683 | 12/1988 | Chang . | |
| 4,969,037 | 11/1990 | Poleschinski . | |
| 5,334,844 | * 8/1994 | Pollard et al. ....................... | 250/330 |
| 5,367,174 | * 11/1994 | Brazile et al. ....................... | 250/572 |
| 5,768,138 | 6/1998 | Ruotolo . | |

FOREIGN PATENT DOCUMENTS

| | | |
|---|---|---|
| 0711995 | 5/1996 | (EP) . |
| 9740367 | 10/1997 | (WO) . |

OTHER PUBLICATIONS

*Patent Abstracts of Japan*, vol. 017, No. 014, Jan. 11, 1993.

* cited by examiner

*Primary Examiner*—Constantine Hannaher
*Assistant Examiner*—Otilia Gabor
(74) *Attorney, Agent, or Firm*—Connie M. Thousand

(57) ABSTRACT

A method and apparatus for the inspection of a substrate provides consistent detection of defects such as cracks, differentiates between different types of defects, and, does not excessively heat the substrate. An infrared radiating source produces infrared energy which illuminates the substrate in a uniform manner at an incident angle. An infrared camera collects a portion of the infrared light which is reflected from the substrate. An image is created from the collected light which includes indicia of the defect. The image is examined as the incident angle is varied for changes in the appearance of the indicia.

7 Claims, 2 Drawing Sheets

METHOD AND APPARATUS FOR INSPECTION OF A SUBSTRATE BY USE OF A RING ILLUMINATOR

BACKGROUND OF THE INVENTION

The present invention relates generally to inspection devices, and more particularly to a device which can perform inspections of a substrate by an infrared imaging technique.

Cracks or defects in a substrate can result in substrate failures or failures in the system in which the substrate is placed. When the substrate is used as a solar cell, the crack or defect has the potential to severely limit the power output of the solar panel which contains the defective solar cell. Once a crack has begun, it is highly probable that it will propagate over time to develop into a more significant crack; therefore, it is important to detect not only large but also small cracks. Flight program specifications typically require few or zero cracks in solar panels many square meters in size.

A well-known method for inspecting solar cells involves illuminating the solar cell from the side with a tungsten halogen lamp and imaging the returned light with an infrared camera. Since this technique requires illuminating the solar cell from one side, it typically results in one side of the solar cell being too bright and the other side being too dim such that the solar cell is not uniformly illuminated. This lack of uniform illumination can mask small cracks, thereby leaving them undetected.

This prior art method also typically requires operating the tungsten halogen lamp at a relatively high intensity level in order to provide sufficient illumination of the entire solar cell. Because a tungsten halogen lamp has a quartz envelope, it strongly absorbs energy in the 2 to 5 micron wavelength range of interest. To compensate for such absorption losses, a tungsten halogen lamp often operates at a relatively high temperature resulting in a large fraction of the light output power having shorter wavelengths. The shorter wavelength radiation, especially in the 1.0 to 2.0 micron range can result in glare due to strong reflections of the solar cell cover glass in the 1.0 to 2.0 micron wavelength range. Additionally, this high intensity level adds heat to the solar cell, which can result in thermal expansion of the cell, closing cracks temporarily during the inspection process such that those cracks avoid detection. Excessive heating of the solar cell can also result in ambiguous cell crack detection since the cell re-radiates the heat which is then imaged by the camera. Features in the image can appear as cracks even though no cracks exist.

In addition, the current method cannot objectively and definitively differentiate surface anomalies from substrate cracks. Surface anomalies are mainly caused by the presence of contaminants, such as solvent stains, on the surface of the substrate. The contaminant is generally not harmful to solar cell performance and typically does not result in a rejection of the solar cell. For the current method, the image of a surface anomaly is typically more diffuse that the image of a cell crack; however, in many cases it is difficult to distinguish between a cell crack and a surface anomaly based solely on the appearance of the image. As a result, reinspection of the cell to distinguish between a crack and a surface anomaly is typically required, resulting in increased inspection time and cost. It is desirable to distinguish surface anomalies from cell cracks to avoid any unnecessary rejection of good cells or unnecessary rework of an otherwise good cell.

What is needed therefore is an apparatus and method for detecting defects in a substrate such as a solar cell which provides consistent detection of defects such as cracks, differentiates between types of defects, and, does not excessively heat the substrate.

SUMMARY OF THE INVENTION

The preceding and other shortcomings of the prior art are addressed and overcome by the present invention which provides an apparatus for detecting a defect in a substrate which includes an infrared radiating source spaced from the substrate and positioned to substantially uniformly illuminate the substrate with infrared light, an infrared camera with a lens positioned to collect the reflected infrared light from the substrate and means for creating an image from the reflected light, the image which including indicia representative of the defect.

In a second aspect, the present invention provides a method for detecting a defect in a substrate, including the steps of illuminating the substrate with an infrared light source in a substantially uniform manner, collecting reflected infrared light from the substrate, producing an image from the reflected infrared light and examining the image for indicia of a defect.

In still another aspect, the present invention provides an apparatus for detecting defects in a substrate and determining the type of each defect which includes an infrared radiating source spaced from the substrate and positioned to substantially uniformly illuminate the substrate with infrared light at an incident angle, an infrared camera with a lens positioned to collect the reflected infrared light from the substrate, means for creating an image from the collected light which includes indicia representative of the defect and means for varying the incident angle.

The foregoing and additional features and advantage of this invention will become apparent from the detailed description and accompanying drawing figures below. In the figures and the written description, numerals indicate the various features of the invention, like numerals referring to like features throughout for both the drawing figures and the written description.

BRIEF DESCRIPTION OF THE DRAWINGS

Reference is now made to the detailed description of the preferred embodiments illustrated in the accompanying drawings, in which.

DETAILED DESCRIPTION OF THE PREFERRED EMBODIMENTS

Figure 1:
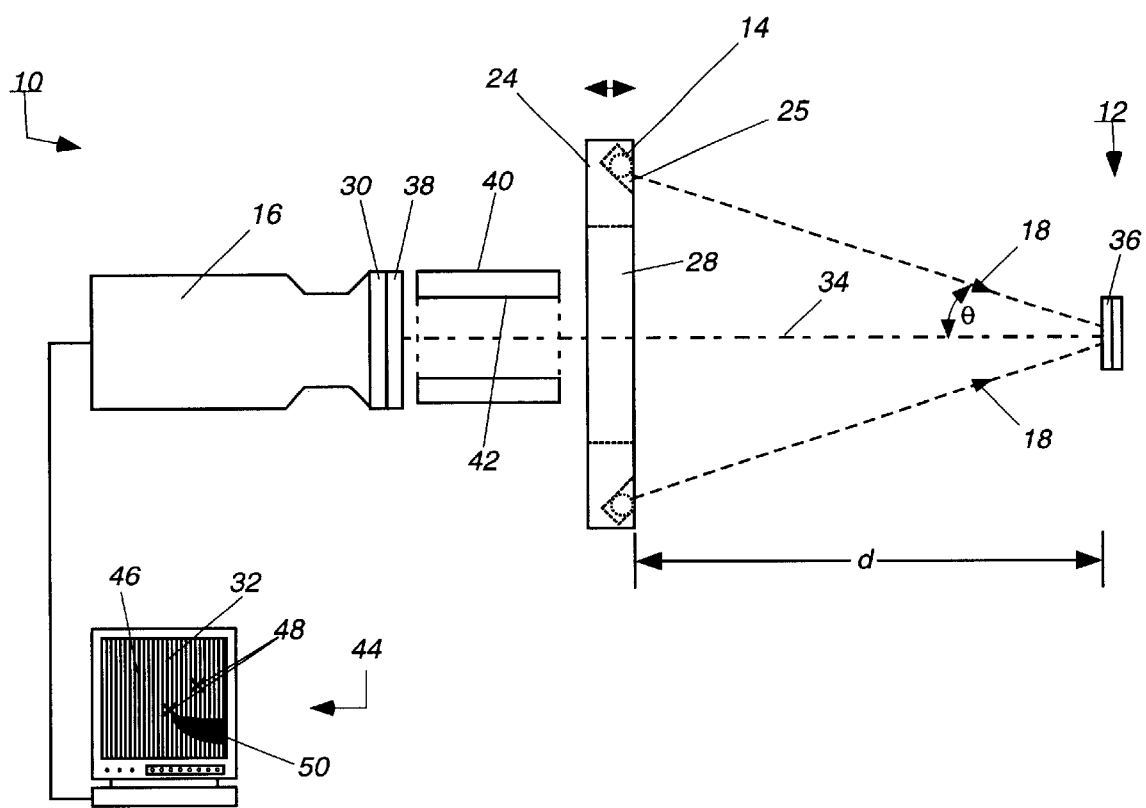
FIG. 1 is a side view of the inspection device in accordance with the preferred embodiment of the present invention.

Referring to FIG. 1, an inspection device 10 for inspecting a substrate 12 and detecting defects such as cracks and surface anomalies is illustrated. The inspection device 10 of the present invention is preferably utilized to inspect solar cells 12 because it provides consistent, accurate detection of cracks and accurate differentiation between cracks, surface anomalies and delamination type defects.

The present invention is not limited to detecting cracks, surface anomalies and delamination type defects in a solar cells, but may also be utilized to detect defects in other substrates such as silicon, gallium arsinide, germanium and other substrates used in integrated circuits or energy collecting devices.

Figure 2:
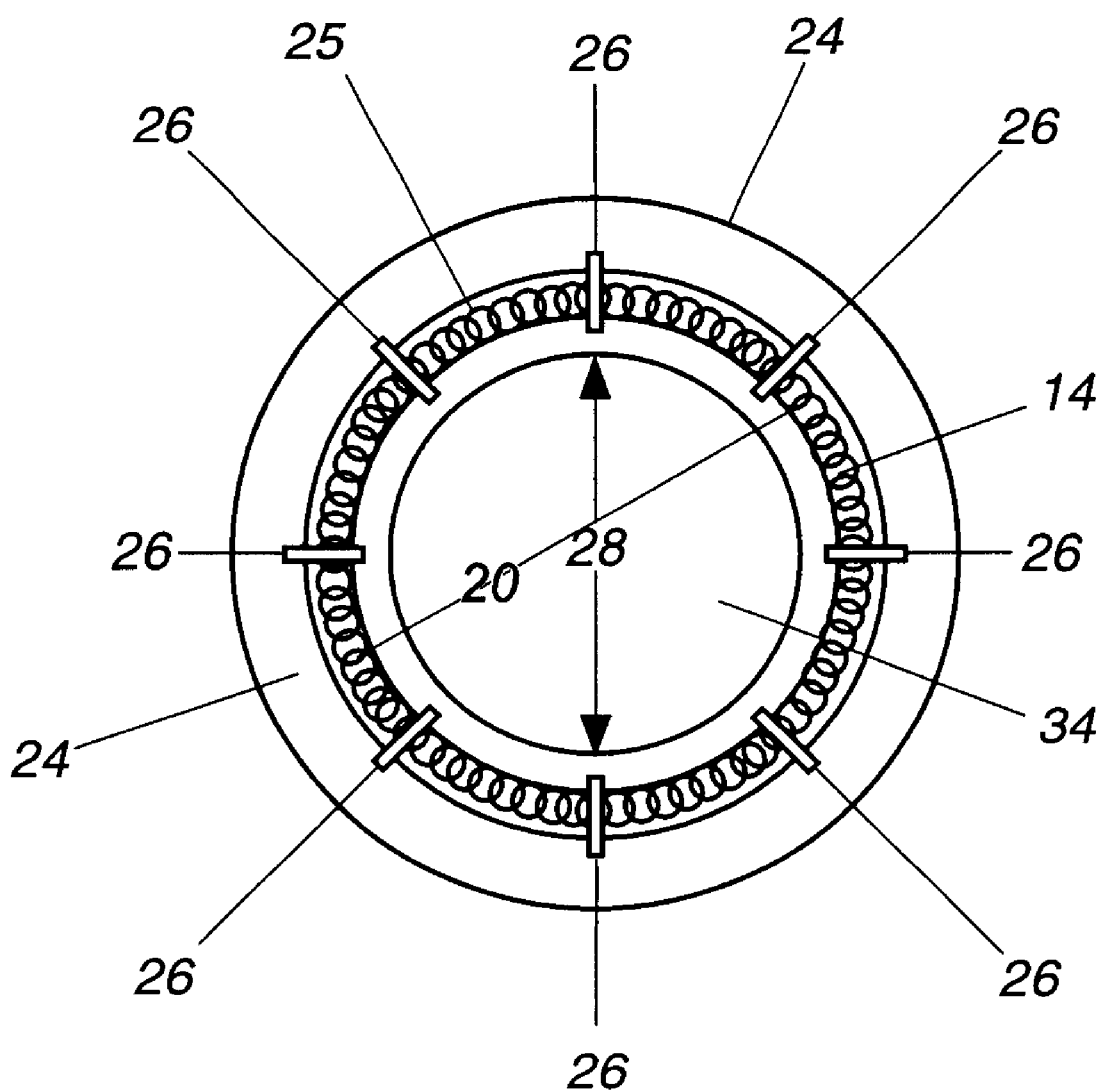
FIG. 2 is a detailed end view of the ring illuminator illustrated in FIG. 1.

As is illustrated in FIGS. 1 and 2, the inspection device 10 includes an infrared radiating source 14 and infrared camera 16. The infrared radiating source 14 produces infrared energy 18 which is utilized to illuminate the substrate 12. The source 14 can be any radiating source 14 which provides uniform illumination of a substrate 12, but it is preferred that the source 14 be a ring illuminator 14 which is a radiating source in the shape of an annulus or a ring. A ring configuration provides a symmetrical radiation pattern such that the substrate 12 is uniformly illuminated from a constant θ angle. As shown in FIG. 2, for the preferred embodiment of the invention, the ring illuminator 14 is comprised of a small diameter heater wire of a material such as nickel/chromium, which is spirally coiled and formed into an annular ring of a first diameter 20. A 14 centimeter first diameter 20 is preferred for ease in handling and for providing good uniform illumination at both a far and a near distance from the substrate 12 (FIG.1). However, the present invention is not limited to a 14 centimeter first diameter 20 (FIG. 2) but may be practiced with different size ring illuminators 14 having a variety of first diameters 20.

Referring to FIGS. 1 & 2, for the preferred embodiment of the invention, the ring illuminator 14 is supported by an insulator 24. The insulator 24 can be formed from any material that has low thermal conductivity and can withstand the temperatures associated with the ring illuminator 14, however, it is preferred that the insulator 24 be fabricated of a transite material. The ring illuminator 14 can be fastened to the insulator 24 by use of ceramic standoffs (not shown); however, it is preferred that the insulator 24 contain a groove 25 in which the ring illuminator 14 is placed. The ring illuminator 14 can be secured into the groove 25 by several fasteners 26 which are preferably fabricated of a ceramic material. An opening 28 is provided in the insulator 24 such that the camera 16 can view the substrate 12 through the opening 28.

Infrared radiation 18 emitted from the ring illuminator 14, is incident on the substrate 12 at an angle θ, and illuminates the substrate 12. The substrate 12 in turn reflects the incident infrared radiation 18 in all directions. The lens 30 of an infrared camera 16 views the substrate 12 through the opening 28 in the insulator 24. A portion of the reflected radiation is incident on the lens of the camera 16 and is captured and collected by the camera 16. The camera 16 provides the means to create an image 32 from the collected reflected infrared light. The lens 30 of the camera 16 is positioned along an axis 34 approximately normal to the substrate 12 such that a substantial amount of surface area of the substrate 12 can be focused within the field of view of the camera 16. The camera 16 preferably has a spectral response that matches the spectral outputs of the ring illuminator 14. One such camera 16 is a platinum-silicide infrared camera 16 such as an Infracam™ made by Inframatrics Inc., located in North Billerica, Mass. The Infracam has a spectral response from a wavelength of 1 to 5 microns. The lens 30 is preferably a close-up lens 30 which can be used to view a portion of the substrate 12 or the entire substrate 12.

Many substrates 12 such as solar cells 12 include a cover glass 36 with a coating that reflects strongly in the 1 to 2.0 micron wavelength range. For such solar cells 12, a long-pass filter 38 may be added to the camera 16 to block the light reflected from the cover glass 36 and reduce any glare from such reflected light. Alternatively, the lens 30 can be made of a germanium material which acts as a filter to block radiation below a 2.0 micron wavelength.

For the preferred embodiment of the invention, a light shield 40 is placed between the lens 30 of the camera 16 and the insulator 24 to shield the camera 16 from any radiation from the ring illuminator 14 and the insulator 24. The light shield 40 can be formed integral with the insulator 24 or as a separate unit. Preferably, the light shield 40 is a tube of polyvinyl chloride material having an interior surface 42 which is non-reflective to infrared light.

For the preferred embodiment of the invention, the camera 16 provides the means to create an image 32 from the collected reflected infrared light. A separate processor, computer, or the like can also provide the means to create and record an image 32. The image 32 is preferably displayed on a monitor 44. If the substrate 12 is a solar cell 12 which is free of cracks and surface anomalies, the image 32 will be uniform in appearance except for the grid structure 46 inherent in the solar cell structure. If the substrate 12 includes defects, the image 32 will display indicia 48 and 50 of the defects.

When inspecting a solar cell 12, for a large distance d and a small incident angle θ, the indicia of both cell cracks 48 and surface anomalies 50 are displayed as dark images. To distinguish between a surface anomaly 50 and a cell crack 48, the ring illuminator 14 is repositioned closer to the solar cell 12 along the axis 34, thereby decreasing the distance d and increasing the incident angle θ. The image 32 is monitored during the movement of the ring illuminator 14. A cell crack 44 will appear dark regardless of the distance and the incident angle θ. On the other hand, a surface anomaly 50 will be displayed as a dark image when the ring illuminator 14 is positioned at a significant distance from the cell 12 such that the cell 12 is illuminated at a small θ angle. The image 50 fades away as the ring illuminator 14 is repositioned closer to the solar cell 12 and the θ angle increases. The image 50 eventually reappears as a bright image as the ring illuminator 14 is further repositioned closer to the solar cell 12 illuminating the solar cell 12 at an even greater θ angle. The image 32 of the surface anomaly 50 appears dark at a θ angle between approximately 20 and 40 degrees, the image fades away at about 45 to 46 degrees and becomes distinctly brighter at about 58 degrees. The present invention thus differentiates surface anomalies 50 from cell cracks 48 and provides excellent, repeatable results when applied to solar cells 12 having textured surface structures, such as high efficiency silicon cells, and can be used for inspection of bare solar cells 12 or solar cells 12 having a cover glass 36.

In addition, the present invention does not excessively heat the substrate 12. A power input (not shown) into the coiled heater wire of the ring illuminator 14 of about 35 Watts typically provides a level of infrared radiation 18 which adequately illuminates a solar cell 12 without a cover glass 36, and, a power input of about 45 Watts typically provides a level of infrared radiation 18 which adequately illuminates a solar cell 12 with a cover glass 36. These power input levels translate to temperatures of the ring illuminator 14 of approximately 325 to 375 degrees Celsius respectively which is significantly lower than the prior art tungsten halogen lamp such that heating of the solar cell 12 is reduced. Therefore, a cell crack 48 can now be detected more consistently with minimal excess heating.

The present invention also allows for a large surface area of a substrate 12 to be illuminated substantially more uniformly when compared to that achieved in the prior art because the present invention provides symmetrical radiation at a constant incident angle θ from all directions resulting in a uniformly illuminated substrate 12.

In addition, the present invention provides a method to differentiate cell cracks 48 from surface anomalies 50. However, the present invention is not limited to detection of cell cracks 48 and surface anomalies 50 but can also detect other types of defects in substrates 12 including delaminations between the substrate 12 and a second material, such as a metallized material, bonded to the substrate 12. Delaminations are displayed as bright images and remain bright with changes in illumination angle θ whereas substrate cracks 48 are displayed as dark images and remain dark with changes in illumination angle θ, surface anomalies 50 are displayed as a dark image which changes to a bright image with increases in illumination angle θ.

It will be appreciated by persons skilled in the art that the present invention is not limited to what has been shown and described hereinabove, nor the dimensions of sizes of the physical implementation described immediately above. The scope of invention is limited solely by the claims which follows.

What is claimed is:

1. An apparatus for detecting a defect in a solar cell comprising:

an infrared annular ring illuminator radiating source spaced from said solar cell and positioned to substantially uniformly illuminate said solar cell with infrared light, said infrared ring illuminator radiating source being spirally coiled heater wire formed into an annular ring and having a first opening;

an insulator coupled to said spirally coiled heater wire for supporting said spirally coiled heater wire, said insulator having a second opening, said insulator positioned such that said solar cell is visible to said camera through said second opening;

an infrared camera with a lens positioned to collect reflected infrared light from said solar cell, said ring illuminator infrared radiating source positioned between said lens and said substrate such that said solar cell is visible to said camera through said first opening; and, means for creating an image from said reflected infrared light, said image including indicia representative of said defect.

2. The apparatus as in claim 1, wherein said insulator further comprises a circular annular groove facing said solar cell, and, said spirally coiled heater wire is positioned within said circular annular groove.

3. An apparatus for detecting defects in a solar cell and for determining a type of said defect comprises:

an infrared ring illuminator radiating source spaced from said solar cell and positioned to substantially uniformly illuminate said solar cell with infrared light at an incident angle;

an infrared camera with a lens positioned to collect reflected infrared light from said solar cell;

means for creating an image from said reflected infrared light, said image including indicia representative of said defect; and, means to change said incident angle, wherein said indicia representative of a surface anomaly type defect is a dark image which changes to a bright image as said incident angle is increased.

4. An apparatus for detecting defects in a solar cell and for determining a type of said defect comprises:

an infrared ring illuminator radiating source spaced from said solar cell and positioned to substantially uniformly illuminate said solar cell with infrared light at an incident angle;

an infrared camera with a lens positioned to collect reflected infrared light from said solar cell;

means for creating an image from said reflected infrared light, said image including indicia representative of said defect; and, means to change said incident angle, wherein said indicia representative of a delamination type defect is a bright image which remains a bright image with said change of said incident angle.

5. A method for detecting a defect in a substrate and for determining at type of said defect comprising the steps of:

illuminating said substrate with an infrared light source in an approximately uniform manner at an incident angle;

collecting reflected infrared light from said substrate;

producing an image from said reflected infrared light;

examining said image for indicia representative of said defect; and, varying said incident angle while continuously monitoring said image for changes in the appearance of the indicia.

6. The method of claim 5, wherein the step of varying said incident angle further comprises the step of varying said incident angle by moving said infrared light source closer to or further away from said substrate.

7. The method of claim 6, wherein the step of varying said incident angle while continuously monitoring said image further comprises the step of changing said incident angle while continuously monitoring said image, a crack type defect producing a dark image at all said incident angles, and, a surface anomaly type defect producing a dark image which changes to a bright image as said incident angle is increased.

* * * * *